Figure 1:
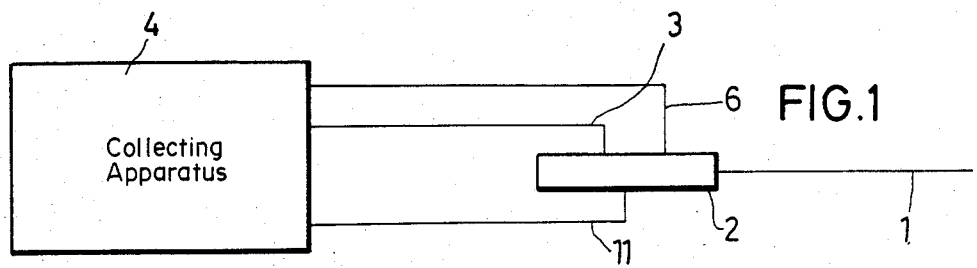

United States Patent [19]

Paulsen

[11] Patent Number: 4,657,027
[45] Date of Patent: Apr. 14, 1987

[54] MEANS FOR TAKING BLOOD SAMPLES FOR THE DIAGNOSIS OF BODILY FUNCTIONS

[75] Inventor: Otto Paulsen, Kiel, Fed. Rep. of Germany

[73] Assignee: Ferring Biotechnik GmbH, Kiel, Fed. Rep. of Germany

[21] Appl. No.: 694,337

[22] Filed: Jan. 24, 1985

[30] Foreign Application Priority Data

Feb. 4, 1984 [DE] Fed. Rep. of Germany ....... 3403957

[51] Int. Cl.$^4$ ............................................. A61B 5/14
[52] U.S. Cl. ..................... 128/762; 128/767; 604/249; 604/327; 73/863.21; 422/81; 436/52
[58] Field of Search ............... 128/672, 762, 767, 769; 604/95, 131, 246, 249, 264, 269, 327; 73/863.01, 863.21, 863.25, 863.82, 864.71, 864.82, 864.83, 864.84, 864.85; 422/81, 82; 436/52, 53

[56] References Cited

U.S. PATENT DOCUMENTS

| | | | |
|---|---|---|---|
| 3,253,468 | 5/1966 | Schultz | 73/864.85 |
| 3,334,018 | 9/1967 | Smythe | 436/53 |
| 3,392,724 | 7/1968 | Cowley | 128/205.21 |
| 3,457,909 | 7/1969 | Laird | 128/672 |
| 3,908,657 | 9/1975 | Kowarski | 128/767 |
| 4,077,395 | 3/1978 | Woolner | 128/762 |

Primary Examiner—Kyle L. Howell
Assistant Examiner—Randy Citrin
Attorney, Agent, or Firm—Pearne, Gordon, McCoy & Granger

[57] ABSTRACT

For diagnosing bodily functions of a patient by analyzing individual, samples several blood samples are taken from the patient automatically in sequence at predetermined time intervals, collected together separately from one another, retained until the completion of all the samples, and then analyzed. The blood samples are fed into a single collecting container one after another in time sequence with the aid of a control valve and are held separated from one another by the introduction of a separating medium between them or they are fed individually in sequence into separate containers. An anti-coagulant prevents the blood samples coagulating before analysis, and so the patient can wear the apparatus for taking the blood samples and can move about and behave normally throughout the sampling sequence.

15 Claims, 6 Drawing Figures

MEANS FOR TAKING BLOOD SAMPLES FOR THE DIAGNOSIS OF BODILY FUNCTIONS

The invention relates to means for taking blood samples for the diagnosis of bodily functions of a patient by analysing individual blood samples, by means of which several blood samples can be taken from the patient one after another at spaced intervals of time, the samples being subsequently analysed for the diagnosis.

For diagnosing bodily functions of a patient it is known to take several blood samples from the patient in succession and to analyse these individual samples in order then to determine whether, and if so which, medicaments must be dispensed to the patient. For example a blood sample is taken from the patient when his stomach is empty and further samples are taken after breakfast and/or after bodily exercise. The time intervals between the taking of the individual samples are very widely different and also inaccurate, so the analysis of the blood samples often cannot give an exact picture of the bodily functions. A further drawback lies in the fact that generally only two, or at most three, blood samples are taken and analysed, to which fact is likewise attributable the fact that the bodily functions of the patient can be only inaccurately ascertained by such a blood analysis. Accordingly, the necessary therapy can also not be determined with sufficient accuracy.

The basis of the invention lies in being able to improve the taking of blood samples for the diagnosis of the bodily functions of the patient in such a way that, in the subsequent analysis of the blood samples taken, there is obtained a very much more accurate picture of the bodily functions of the patient than was hitherto possible.

This problem is solved according to the invention by means which comprise a catheter for permanent connection to the patient, a flexible pipe connected to it, a pump which is switched on and off according to a predetermined programme and at least one container for the blood samples (or program), this container being exchangeable with the pipe and the catheter and being possibly in the form of a flexible pipe. This apparatus is in a form which can be worn and accordingly can be secured to the patient for the duration of the blood sampling. It is only necessary for the doctor to insert the catheter at the start and set the programme for controlling the pump and then to switch it on. The taking of the blood samples occurs automatically in the desired sequence and over the desired time duration, and the patient can move about freely. On completion of the sampling period the patient returns to the doctor who is treating him, and the doctor releases the catheter and removes the apparatus from the patient.

By means of the apparatus according to the invention, therefore, a plurality of blood samples can be taken from a patient automatically at predetermined time intervals, the samples can be collected separately from one another, kept on the patient until after completion of the blood-sampling sequence, and subsequently analysed. In contrast to the hitherto usual taking of blood samples, carried out by hand in the clinic or the doctor's surgery, and at time intervals of more or less chance duration, in the arrangement according to the invention the taking of the samples occurs automatically at accurately predetermined time intervals, for example at intervals of half an hour at a time, and furthermore in general a larger number of samples is taken than was hitherto usual. Accordingly the sampling of the blood can be spread over a larger period of time, for example twenty-four hours. The analysis of the many samples thus obtained gives a very much more accurate picture of the bodily functions of a patient than is obtained in the hitherto orthodox diagnosis using only a few blood samples. Therefore the doctor can also determine very much better what medicaments should be dispensed to a patient and in what quantities and at what time intervals, for the necessary therapy.

Because the blood samples taken from the patient are first collected together and retained separately from one another until the desired number of samples for the analysis has been taken, a mobile sampling of the blood is possible, that is to say, the patient can move about freely as the samples are being taken, because only at the end of the sequence of taking all the blood samples do they have to be given to the doctor who is to deal with them. Up to now the taking of blood samples at time intervals extending over a whole day has been possible in practice only by remaining at the clinic. However, by remaining at the clinic, the natural behaviour of the patient cannot be reproduced as the usual loads involved in physical work or even in normal working at a desk are lacking.

So that the individual blood samples taken from the patient one after another do not congeal before analysis an anti-coagulant is preferably added to them. For example, directly after sampling, the blood is mixed, through a valve, with an added anti-coagulant. Another possibility is to emulsify an anti-coagulant with a separating medium, e.g. silicone oil. In this arrangement the wall of the container which receives the samples is coated with the anti-coagulant so that the blood with which it is filled does not congeal.

So that the individual blood samples can be reliably collected and stored in a container separately from one another, an inert separating medium, for example, silicone-based or if possibly also gas or air, is introduced into the collecting container between the individual samples, forming a separating layer between the individual samples and effectively preventing any mixing of the samples with one another. Alternatively the individual blood samples could be collected in separate containers if the number of samples needed for the analysis is not too large.

The collected samples can then be sent to the laboratory for analysis.

Preferably the pump comprises a roller pump (peristaltic pump) acting on the flexible pipe. The collecting container can be made of a transparent flexible material so that under some circumstances the blood samples do not even need to be removed from the collecting container for the analysis. The pipe-shaped collecting container can be rolled up on a roller or drum so that a substantial length of tube for a large number of samples can be contained in as small a space as possible.

In one embodiment of the invention the apparatus can be provided with means for adding the separating medium between the individual blood samples and if necessary a further device for adding an anti-coagulant, and these devices could each incorporate a pump such as a peristaltic pump.

Generally it is sufficient to have a single device for adding a separating medium. However one can envisage situations in which a second coagulant-adding device is necessary, namely when the coagulant reacts with the material under investigation and one has to employ a different anti-coagulant which cannot be emulsified with the separating medium such as silicone oil.

Where the successively taken individual blood samples are each received in a separate container and kept until analysis no separating medium is necessary and so a device for adding it is not required. However even in this case it is necessary to put an anti-coagulant into the individual containers so that the blood samples do not coagulate before analysis. For example there is provided for this purpose an adding device which puts the anti-coagulant into the container directly before or during the entry of a blood sample.

A further possibility lies in preparing the inside walls of the individual containers beforehand with an anti-coagulant or putting the anti-coagulant into the the containers in question in sufficient quantity beforehand. In this case a special adding device can be omitted.

The adding device preferably includes a change-over control valve which connects the container in question in a controlled sequence alternately to the catheter and to a reservoir container for the inert separating medium and/or anti-coagulant. This control valve can be changed over in common with the roller pump by a micro-computer in accordance with a predetermined programme. For example it is a three-way valve, e.g. a slide valve or a three-way cock.

In the case of a slide valve the slide of the valve is for example controlled electromagnetically, but other possibilities for controlling it can be envisaged, for example by the use of compressed air possibly combined with a return spring, or with the aid of a toothed rack drive.

It is also possible for the change-over control valve to contain a single passage which, in accordance with the position of the control element, such as the slide, connects the catheter at will to a number of containers for receiving respective individual blood samples and a container for receiving blood waste. When such a control valve is used there is no need to employ a separating medium because the individual blood samples are put into separate containers and retained in them. The quantities of blood remaining in the catheter and in the pipe to the control valve, as well as in the control valve itself, between the individual blood-sampling sequences are fed into the collecting container as waste at the beginning of the taking of a further blood sample, before the freshly taken blood sample, which has displaced the residue of the previously removed sample through the catheter and the control valve into the waste container, is fed into the container provided for it by subsequent switching-over of the control valve.

Such apparatus is suitable for taking blood samples in limited numbers. The actuation of the control slide can be achieved for example by a toothed rack drive.

The invention is also suitable for measuring the rise in blood level of predetermined bodily materials after dosing with medicaments, in particular for scientific investigations. For example most of the body's hormones have a different discharge rhythm which hitherto has been known only for a few hormones because of the difficulty of blood-sampling. The present invention makes it possible to determine the separation rhythm of all human hormones with an acceptable outlay.

Figure 2:
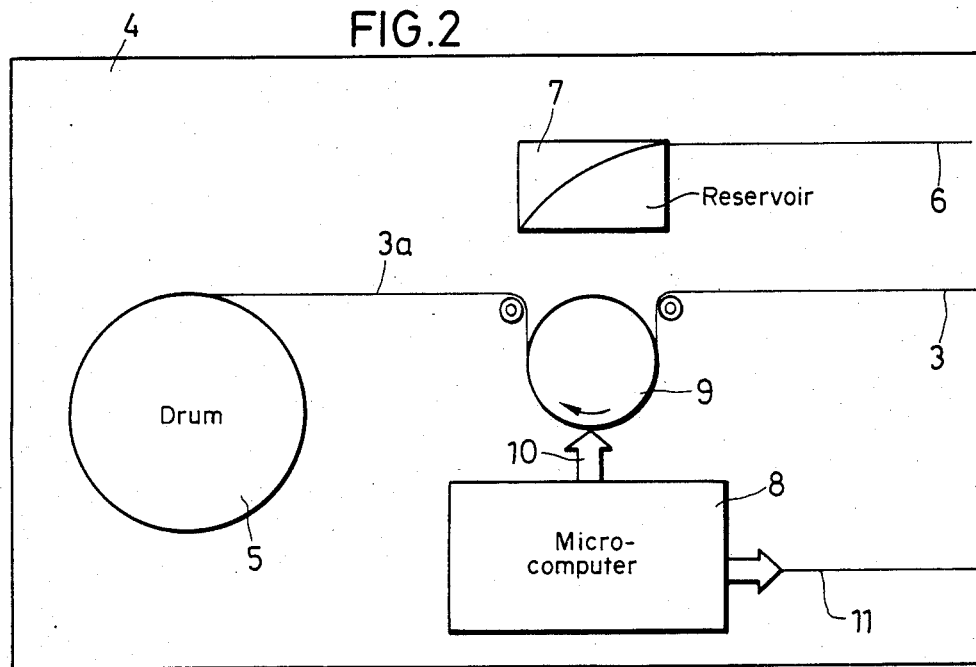
Figure 3A:
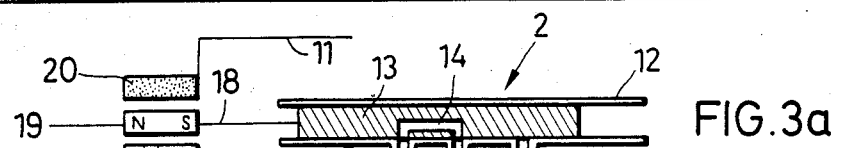
Figure 3B:
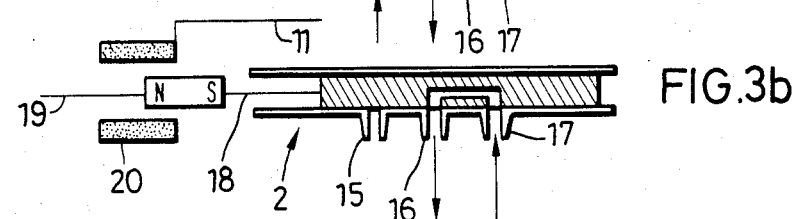
Figure 4:
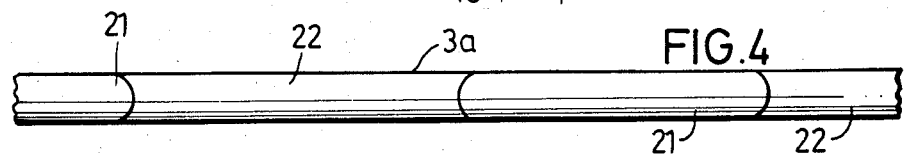
Figure 5:
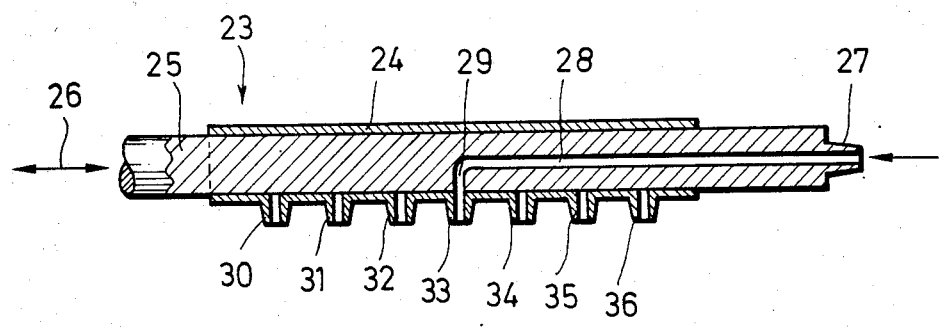
Figure 6:
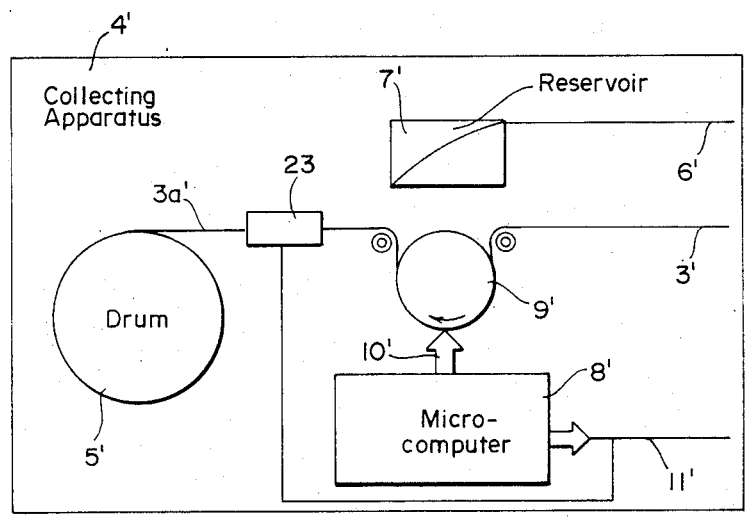

An embodiment of apparatus for taking a plurality of blood samples in pre-programmed sequence in accordance with the invention is illustrated in the drawing by way of example, and in the drawing:

FIG. 1 is an overall view of the apparatus;
FIG. 2 shows details of the collecting equipment of the apparatus;
FIG. 3a shows one embodiment of the control valve in the first of two different positions of operation;
FIG. 3b shows the control valve in the second of the two different positions;
FIG. 4 is a partial side view of a pipe-shaped collecting container filled with blood samples and an inert separating fluid present between them;
FIG. 5 shows another embodiment of the control valve; and
FIG. 6 is similar to FIG. 2 and shows the incorporation of the control valve of FIG. 5 in the apparatus.

As shown in FIGS. 1 and 2 the apparatus has a catheter 1 for connection to the patient, connected through a control valve 2 to a flexible pipe 3 which leads into a collecting apparatus 4 and there, as a collecting container 3a for blood samples, it is wound up on a drum 5.

Connected to the valve 2 there is also a pipe 6 through which an inert fluid, for example silicone oil, serving as a separating medium is fed from a reservoir 7 to the valve 2 and from there can be fed into the pipe 3.

In the collecting apparatus 4 there is a micro-computer 8 provided with a keyboard, not shown, and a display, and it serves for controlling the valve 2 and a peristaltic pump 9 acting on the pipe 3. For this purpose the micro-computer 8 is connected to the pump 9 through an electric lead 10 and to the valve 2 through a further electric lead 11. With the aid of the keyboard and the display a program can be fed into the micro-computer for taking blood samples at predetermined time intervals. The micro-computer 8 then sets the pump 9 going at the predetermined times in order to take a blood sample from the patient through the catheter 1. The valve 2 is then set so that the catheter 1 is connected to the pipe 3.

At the end of each blood-sampling process the valve 2 is changed over so as to connect the pipe 6 to the pipe 3 and to suck fluid separating medium from the reservoir 7 into the pipe 3 and its extension 3a which forms the collecting container. Thereupon the pump 9 is switched off unless a further blood sample is to be taken immediately afterwards.

The pump 9 delivers the individual blood samples and the separating medium present between them into the multi-turn tube-like collecting container 3a wound up on the drum 5, and on completion of the blood-sampling process it is removed from the collecting apparatus 4 so that the blood samples can be analysed in a normal manner in the laboratory.

As shown in FIGS. 3a and 3b the valve 2 is a slide valve comprising a barrel 12 with a piston-shaped slide 13 containing a passage 14 which, according to the position of the piston 13 in the barrel 12, connects together respective pairs of three connecting spigots 15, 16 and 17. The spigot 15 leads to the pipe 6, the spigot 16 to the pipe 3 and the spigot 17 to the catheter 1.

The piston slide 13 is provided with a piston rod 18, on the free end of which there is a permanent magnet 19 co-operating with an electric winding 20. The coil 20 is energised by pulses through the electric connection 11 from the micro-computer 8 so that the magnet 19 and thereby the slide 13 is displaced between the two positions illustrated in FIGS. 3a and 3b.

In the position shown in the FIG. 3a the passage 14 connects the spigots 15 and 16 so that the pipe 6 is connected to the pipe 3. In the position shown in FIG.

3b the passage 14 connects the spigots 16 and 17, thereby connecting the pipe 3 to the catheter 1. Accordingly when the pump 9 is running, either inert separating medium is drawn from the reservoir 7 (FIG. 3a) or blood is drawn from the catheter 1 into the pipe 3 (FIG. 3b). With such apparatus, with uniform time intervals between the blood samples, the first part of a supply of blood which is delivered is still from the previously taken sample. In order to obtain reliable separation between the samples, the sampling is accordingly controlled in such a way that on each occasion two blood samples are taken shortly one after the other and only the second, i.e. uncontaminated, blood sample is employed for analysis. The piston slide 13 of the valve 2 can be displaced relatively easily, namely by reversing the polarity of the electromagnet 20, by the action of compressed air or also by the use of a toothed gear drive.

FIG. 4 shows how individual blood samples 21 present in the tubular collecting container 3a, as compared with the pipe 3 and the collecting container 3a, have a higher surface tension than the intervening separating cushions 22 of inert fluid such as silicone oil. Accordingly the pump 9 has no influence on separation between the successive blood samples 21, i.e. even in the region of the pump 9 successive samples 21 cannot run together and also cannot mix with the separating medium.

The control valve 23 illustrated in FIG. 5 has a barrel 24 serving as a housing in which a piston-shaped slide 25 is guided to slide axially. At the left hand end of the slide 25, as viewed in FIG. 5, there is a drive which has been omitted in the interests of simplifying the drawing and is indicated simply by a double arrow 26. At the opposite end of the slide 25 there is a connecting spigot 27 which is connected to communicate with the catheter 1 via pipe 3' and roller pump 9' in order to allow controlled blood-sampling in the manner described. (The same reference numerals are used in FIG. 6 with the addition of prime designations.)

The slide 25 contains a passage 28 starting from the spigot 27 and leading longitudinally through the slide to end in a radial branch 29. This radial branch 29, according to the position of the slide 25 in the cylinder 24, makes a connection to one of a number of spigots 30-36 on the cylinder 24, to which the individual containers for receiving the blood, not shown, can be detachably connected. For example a collecting container for blood waste is connected to the spigot 30 whilst the spigots 31-36 can have a total of six separate containers for receiving individual blood samples detachably connected to them.

Using such a valve it is possible to collect the blood samples from the patient individually so that no separating medium is needed. The contaminated quantities of blood present in the apparatus between the individual samples provided for the analysis are always conducted through the spigot 30 to the associated container as waste.

I claim:

1. A blood sampling means for automatically taking blood samples from a patient and separately storing the blood samples for subsequent analysis, said blood sampling means comprising a catheter for permanent connection to a patient throughout a preselected time period, a flexible pipe means connected to said catheter, a reservoir of inert separating fluid and/or anti-coagulent fluid adapted to be connected to said pipe means, a pump operably connected to said pipe means to withdraw blood samples from said patient through said catheter and fluid from said reservoir and to pump said blood samples and fluid through said pipe means, said pipe means including a flexible container tube for receiving and storing said blood samples and fluid, drum means for mounting said flexible container tube in a coil-configuration, valve means for connecting said fluid container tube alternately to said catheter and to said reservoir for flowing blood samples and portions of said fluid into said fluid container tube, and control means for switching said pump on and off and for operating said valve means to automatically take a plurality of blood samples from said patient at spaced intervals during said time period in accordance with a predetermined programme.

2. Means as set forth in claim 1, wherein said control means comprise a programmable microcomputer.

3. Means as set forth in claim 2, wherein said pump is a peristaltic pump which acts on said flexible pipe means.

4. Means as set forth in claim 3, wherein said flexible pipe means is a flexible hose having a first hose portion which is connected to said catheter and a second hose portion which provides said flexible container tube.

5. Means as set forth in claim 4, wherein said second hose portion is transparent.

6. Means as set forth in claim 3, wherein said valve means is a three-way valve.

7. Means as set forth in claim 6, wherein said three-way valve is a slide valve.

8. Means as set forth in claim 7, wherein said slide valve includes a slide and said means also includes electro-magnetic means for electromagnetically actuating said slide.

9. Means as set forth in claim 1 wherein said pipe means include a plurality of said flexible container tubes, said drum means having mounted thereon each of said flexible container tubes in a coil configuration, said valve means including first valve means for alternately connecting said pipe means to said catheter and to said reservoir, and second valve means for connecting said pipe means selectively to each of said flexible container tubes.

10. Means as set forth in claim 9, wherein one of said flexible container tubes is a waste storage container tube for receiving contaminated quantities of blood present in the blood sampling means prior to taking a blood sample for storage.

11. Means as set forth in claim 9, wherein said control means comprise a programmable microcomputer.

12. Means as set forth in claim 11, wherein said pump is a peristaltic pump which acts on said flexible pipe means.

13. Means as set forth in claim 9, wherein said second valve means includes a port associated with each of said flexible tube containers and is operable to selectively connect said catheter to each of said ports.

14. Means as set forth in claim 13, wherein said valve means is a slide valve.

15. Means as set forth in claim 14, wherein said slide valve includes a slide and said means also includes electro-magnetic means for electromagnetically actuating said slide.

* * * * *